United States Patent
Call (10) Patent No.: US 8,653,469 B1
(45) Date of Patent: Feb. 18, 2014

(54) K-ALPHA PROBE FOR DETECTION OF PHOTON EMISSIONS

(71) Applicant: Devicor Medical Products, Inc., Sharonville, OH (US)

(72) Inventor: John D. Call, Waverly, OH (US)

(73) Assignee: Devicor Medical Products, Inc., Sharonville, OH (US)

( * ) Notice: Subject to any disclaimer, the term of this patent is extended or adjusted under 35 U.S.C. 154(b) by 0 days.

(21) Appl. No.: 13/709,794

(22) Filed: Dec. 10, 2012

Related U.S. Application Data (63) Continuation of application No. 12/727,441, filed on Mar. 19, 2010, now Pat. No. 8,344,331.

(60) Provisional application No. 61/162,221, filed on Mar. 20, 2009.

(51) Int. Cl.
*G01T 1/16* (2006.01)
*G01T 1/161* (2006.01)
*G01T 1/167* (2006.01)
*G01T 1/202* (2006.01)

(52) U.S. Cl.
USPC ............ 250/370.12; 250/370.13; 250/370.11; 600/436; 600/431

(58) Field of Classification Search
USPC ........ 250/370.01–370.15, 367, 393; 600/436, 600/431
See application file for complete search history.

(56) References Cited

U.S. PATENT DOCUMENTS

| | | | |
|---|---|---|---|
| 3,967,122 A * | 6/1976 | Ashe et al. ................... 250/367 |
| 4,782,840 A | 11/1988 | Martin, Jr. et al. |
| 4,786,810 A | 11/1988 | Shulman et al. |
| 4,801,803 A | 1/1989 | Denen et al. |
| 4,889,991 A | 12/1989 | Ramsey et al. |
| 4,893,013 A | 1/1990 | Denen et al. |
| 5,070,878 A | 12/1991 | Denen |
| 5,151,598 A | 9/1992 | Denen |
| 5,383,456 A | 1/1995 | Arnold et al. |
| 5,429,133 A | 7/1995 | Thurston et al. |
| 5,441,050 A | 8/1995 | Thurston et al. |
| 5,475,219 A | 12/1995 | Olson |
| 5,495,111 A | 2/1996 | Thurston et al. |
| 5,682,888 A | 11/1997 | Olson et al. |
| 5,732,704 A | 3/1998 | Thurston et al. |
| 5,857,463 A | 1/1999 | Thurston et al. |
| 5,916,167 A | 6/1999 | Kramer et al. |
| 5,919,167 A | 7/1999 | Mulhauser et al. |
| 5,928,150 A | 7/1999 | Call |
| 5,987,350 A | 11/1999 | Thurston |

(Continued)

*Primary Examiner* — David Porta
*Assistant Examiner* — Yara Green
(74) *Attorney, Agent, or Firm* — James R. Eley; Michael A. Forhan; Eley Law Firm Co. LPA (57) ABSTRACT

A probe for detecting K-alpha photon emissions. A housing has an aperture at an end. A detector crystal is situated within the housing adjacent to the housing aperture. An energy conversion device is situated within the housing between the detector crystal and the aperture. The energy conversion device is made from a predetermined material configured to convert energy directed through the housing aperture from a source of primary photon emission radiation to a corresponding secondary K-alpha emission within a predetermined emission energy acceptance window. A power supply is coupled to the detector crystal and is configured to establish a polarized electrical field between the anode and the cathode of the detector crystal. The detector crystal receives the K-alpha emission and generates an electrical signal representative of the amount of target emissions received through the housing aperture.

19 Claims, 8 Drawing Sheets

(56) References Cited

U.S. PATENT DOCUMENTS

| | | |
|---|---|---|
| 6,093,381 A | 7/2000 | Triozzi et al. |
| 6,144,876 A | 11/2000 | Bouton |
| 6,153,883 A | 11/2000 | Arai |
| 6,191,422 B1 | 2/2001 | Thurston |
| 6,202,198 B1 | 3/2001 | Bibyk |
| 6,204,505 B1 * | 3/2001 | Call .................. 250/370.01 |
| 6,218,669 B1 | 4/2001 | Call |
| 6,222,193 B1 | 4/2001 | Thurston et al. |
| 6,259,095 B1 | 7/2001 | Bouton et al. |
| 6,272,373 B1 | 8/2001 | Bouton |
| 2010/0177868 A1 | 7/2010 | Smith |

* cited by examiner

| User Settings for High Energy Probes | | | | | | | | | | |
|---|---|---|---|---|---|---|---|---|---|---|
| | | Box | RadioNuclide | Setting | Energy | Low threshold | High Threshold | Peak | LT | HT |
| PET | $^{18}$F | 1 | $^{18}$F | User 4 | 511 | 460 | 530 | 527 | 475 | 546 |
| | $^{18}$F | 1 | $^{18}$F | User 1 | 511 | 500 | 550 | 527 | 516 | 567 |
| New PET | $^{18}$F | 1 | $^{18}$F | User 2 | 511 | 460 | 530 | 445 | 400 | 462 |
| | $^{124}$I | 2 | $^{18}$F | User 1 | 603 | 540 | 650 | 525 | 470 | 566 |
| 3000 | $^{18}$F | 1 | $^{18}$F | User 3 | 511 | 460 | 530 | 289 | 260 | 300 |
| | $^{124}$I | 2 | $^{18}$F | User 2 | 603 | 540 | 650 | 341 | 305 | 365 |
| Thurston | $^{124}$I/$^{18}$F | 2 | $^{18}$F | User 3 | | | | 78 | 60 | 95 |

| User Settings BOX 1 | | | | | | | | | | |
|---|---|---|---|---|---|---|---|---|---|---|
| | | Box | RadioNuclide | Setting | Energy | Low threshold | High Threshold | Peak | LT | HT |
| PET | $^{18}$F | 1 | $^{18}$F | User 4 | 511 | 460 | 530 | 527 | 475 | 546 |
| | $^{18}$F | 1 | $^{18}$F | User 1 | 511 | 500 | 550 | 527 | 516 | 567 |
| New PET | $^{18}$F | 1 | $^{18}$F | User 2 | 511 | 460 | 530 | 445 | 400 | 462 |
| 3000 | $^{18}$F | 1 | $^{18}$F | User 3 | 511 | 460 | 530 | 289 | 260 | 300 |

| User Settings BOX 2 | | | | | | | | | | |
|---|---|---|---|---|---|---|---|---|---|---|
| | | Box | RadioNuclide | Setting | Energy | Low threshold | High Threshold | Peak | LT | HT |
| New PET | $^{124}$I | 2 | $^{18}$F | User 1 | 603 | 540 | 650 | 525 | 470 | 566 |
| 3000 | $^{124}$I | 2 | $^{18}$F | User 2 | 603 | 540 | 650 | 341 | 305 | 365 |
| Thurston | $^{124}$I/$^{18}$F | 2 | $^{18}$F | User 3 | | | | 78 | 60 | 95 |

K-ALPHA PROBE FOR DETECTION OF PHOTON EMISSIONS

This application is a continuation of U.S. patent application Ser. No. 12/727,441, filed Mar. 19, 2010, which claims priority to U.S. provisional patent application No. 61/162,221, filed Mar. 20, 2009. The entire contents of each of these applications is expressly incorporated herein by reference thereto.

FIELD

The present invention relates generally to nuclear detection system instrumentation, including, but not limited to, a probe for use in the intra-operative detection of gamma or other X-ray emissions or as an adjunct to positron emission tomography (PET).

BACKGROUND

Procedures for the treatment of cancer generally have been based upon the natural history of tumor spread, and thence, upon operative surgical and non-surgical options available to the physician. Surgical operative options generally have looked to the pre-, peri-, intro- and post-surgical physical identification and surgical reduction of tumors, but more recently also to the staging of the cancer's progression through the identification and evaluation of tissue to which the cancer may spread. A variety of techniques have been brought to bear in the art with the purpose of aiding the surgeon in detecting and localizing neoplastic tissue as part of these surgical procedures. ("Neoplastic tissue," for the present purposes, often is referred to as cancerous tissue, though malignant tumor and malignant tumor cells also are found in the terminology of the art. The term "neoplastic tissue" includes all of these.) Typically, large tumors are readily located by the surgeon by visualization prior to surgery (via imaging mechanisms) and at the operating theater, and, in particular, through palpation, i.e., the feel of tumor as opposed to that of normal tissue. To increase operative success, however, it is necessary for the surgeon to locate "occult" tumor, i.e., tumor which cannot be found by preoperative imaging or the conventional surgical procedures of sight and feel. Failure to locate and remove such occult tumor generally will result in the continued growth of cancer in the patient, a condition often referred to as "recurrent" cancer.

It is generally also thought that the spread of certain types of solid tumor cancers is caused by the migration (or draining) of tumor cells from the initial tumor to nearby lymph nodes and eventually to other vital sites via the lymphatic system. Cancer surgeons and medical oncologists believe the determination of whether a patient's primary tumor has spread to the lymph nodes is a major determinant of a patient's long-term prognosis. The spread of cancer to the patient's lymph nodes is established by the examination of the nodes by pathology to determine if tumor cells are present. If tumor cells are determined to be present in the lymph nodes, the patient's stage or severity of disease is increased. Surgeons perform procedures to identify the draining node(s) through the injection of a radioactive tracing agent at the site of the primary tumor. Following injection, the tracing agent follows the drainage path of the tumor to the nearest lymph node or nodes, referred to as the "sentinel node(s)." A gamma detection device is used to detect the path of the tracing agent. Since the lymph nodes are connected, oncologists believe that if the sentinel nodes show no sign of malignancy, then the downstream nodes in the pathway are likely to be clear of disease. As such, the removal of other nearby lymph nodes would be clinically unnecessary. Therefore, the ability to rapidly locate and biopsy sentinel nodes provides vital information to the physician in determining if the cancer has spread or if it is localized to the site of the primary tumor.

Recent technologies now allow the surgeon, via a combination of both isotopically labeled drugs and hand-held radiation detection devices, to provide enhanced surgical evaluation of tumor dissemination, e.g., removal of primary tumor-associated lymph nodes. Such surgical radiation detection instrumentation is comprised generally of a hand-held probe which is in electrical communication with a control console via a flexible cable or, more recently, via wireless communication. This control console is located within the operating room facility but out of the sterile field, while the hand-held probe and forward portions of any associated cable are located within that field. The hand-held radiation detecting probe is preferably relatively small and performs in conjunction with a semiconductor detector such as cadmium zinc telluride (CZT) or a scintillating material including, but not limited to, cesium iodide. Example instrumentation may be found in U.S. Pat. No. 4,782,840, the disclosure of which is expressly incorporated herein by reference.

A drawback of currently available devices related to the detection of higher energy isotopes, however, is the need for high density and/or thick semiconductor or scintillating detectors to generate the requisite instrumentation signals. Such semiconductor detectors require a relatively high bias voltage to achieve rapid charge migration and avoid charge entrapment in areas of impurity in the detector. As a result, a significant amount of insulation is required to mitigate the risk of electrical shock and to prevent electrical insulation breakdown within the probe. Consequently, the detecting probe is physically larger than is optimum, precluding its use in many situations. The sensitivity of such devices may be limited as well.

Radioactive sources have previously been detected directly at whatever energy levels the source of radiation is producing by using detectors comprised of semiconductor (e.g., cadmium-zinc-telluride) or scintillating (e.g., cesium iodide) materials. An output signal is produced when an incoming photon collides with material within the detector. The higher the energy level of the primary source of radiation, the more incoming photons can pass completely through the detector without colliding with any material, thus producing no output from the detector. For this reason, high-energy detectors have necessarily been thick enough and dense enough to assure that a sufficient number of collisions occur to provide usable detector sensitivity. This characteristic of the detector is often referred to as "stopping power" or "absorption efficiency"

SUMMARY

The present invention is a system and method for detecting emissions from radioactive substances during surgical or other procedures and processes, or when there is any need for such evaluation on any scale. This is accomplished by employing a "K-alpha" secondary emission response exhibited by select materials when said materials are bombarded with photons emitted by radiation sources, such as radio-labeled targeting agents. The K-alpha response is produced when a "primary photon emission" from a target source of radiation stimulates the select material, causing the material to fluoresce with secondary emissions at a fixed lower energy level. The select material, when placed between a target source of primary photon emissions and a detector, in effect converts the photon emissions of the target radiation source to secondary emissions at a lower energy level. The detection of this lower energy level greatly increases detector efficiency and obviates the need to employ relatively thick detector crystals. The energy level of the K-alpha response is fixed for a given material and is always lower than the energy level of the excitation radiation that caused it.

An object of the present invention is a probe for detecting K-alpha photon emissions. A housing has an aperture at an end. A detector crystal having a cathode, an anode spaced apart from the cathode, and an edge extending between the cathode and the anode is situated within the housing adjacent to the housing aperture. An energy conversion device is situated within the housing between the detector crystal and the aperture. The energy conversion device is made from a predetermined material configured to convert energy directed through the housing aperture from a source of primary photon emission radiation to a corresponding secondary K-alpha emission within a predetermined emission energy acceptance window. A power supply is coupled to the detector crystal and is configured to establish a polarized electrical field between the anode and the cathode of the detector crystal. The detector crystal receives the K-alpha emission and generates an electrical signal representative of the amount of target emissions received through the housing aperture.

Another object of the present invention is a probe for detecting K-alpha photon emissions according to still another embodiment. A housing has an aperture at an end. An energy conversion device is situated within the housing proximate the aperture. The energy conversion device is made from a predetermined material configured to convert energy directed through the housing aperture from a source of primary photon emission radiation to a corresponding secondary K-alpha emission within a predetermined emission energy acceptance window. A detector crystal has a cathode, an anode spaced apart from the cathode, and an edge extending between the cathode and the anode. The detector crystal is situated within the housing between the housing aperture and the energy conversion device. A power supply is coupled to the detector crystal and is configured to establish a polarized electrical field between the anode and the cathode of the detector crystal. The detector crystal receives the K-alpha emission and generates an electrical signal representative of the target emissions received through the housing aperture.

Yet another object of the present invention is a probe for detecting K-alpha photon emissions according to still another embodiment. The probe comprises a housing having an aperture at an end. A first and a second energy conversion device are situated within the housing, the first and second energy conversion devices being made from a predetermined material configured to convert energy directed through the housing aperture from a source of primary photon emission radiation to a corresponding secondary K-alpha emission within a predetermined emission energy acceptance window. A detector crystal having a cathode, an anode spaced apart from the cathode, and an edge extending between the cathode and the anode is situated within the housing between the first and second energy conversion devices. A power supply is coupled to the detector crystal and is configured to establish a polarized electrical field between the anode and the cathode of the detector crystal. The detector crystal receives the K-alpha emission and generates an electrical signal representative of the amount of target emissions received through the housing aperture.

BRIEF DESCRIPTION OF THE DRAWINGS

Further features of the inventive embodiments will become apparent to those skilled in the art to which the embodiments relate from reading the specification and claims with reference to the accompanying drawings, in which:

DETAILED DESCRIPTION

In the discussion that follows, the teachings of U.S. Pat. Nos. 6,272,373, 6,259,095, 6,222,193, 6,218,669, 6,204,505, 6,202,198, 6,191,422, 6,144,876, 6,093,381, 5,987,350, 5,928,150, 5,916,167, 5,857,463, 5,732,704, 5,682,888, 5,495,111, 5,475,219, 5,441,050, 5,429,133, 5,383,456, 5,151,598, 5,070,878, 4,893,013, 4,889,991, 4,801,803 and 4,782,840 are incorporated herein in their entirety by reference thereto. Furthermore, like reference numerals are used to refer to like structures in the various figures.

Figure 1:
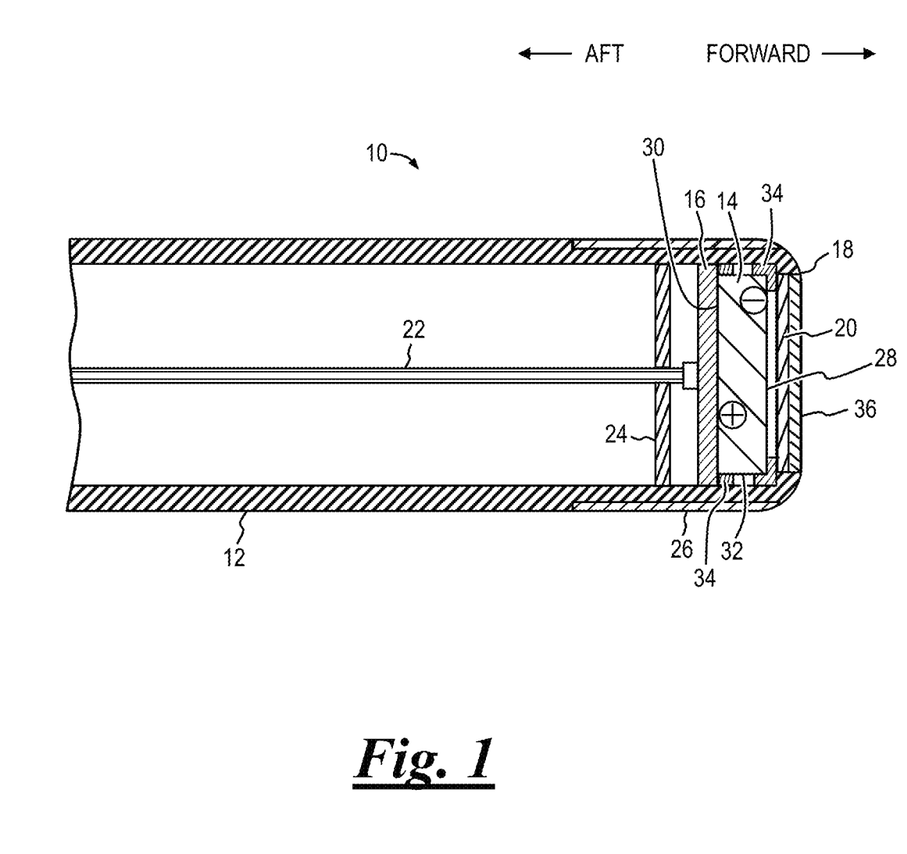
FIG. 1 is a view in section of a probe for detection of photon emissions according to an embodiment of the present invention.

The general arrangement of a probe 10 for detecting photon emissions is shown in FIG. 1 according to an embodiment of the present invention. Probe 10 comprises a housing 12. A detector crystal 14, which may be mounted to a printed circuit board 16, is disposed within housing 12 proximate an aperture 18 of the housing. An energy conversion device ("ECD") 20 is coupled to housing 12, proximate detector crystal 14 and substantially closing off aperture 18. A set of leads 22 provides electrical communication with printed circuit board 16 and detector crystal 14, leads 22 being connected to a suitable radiation detection apparatus, such as (but not limited to) those disclosed in one or more of the aforementioned patents.

In some embodiments it may be desirable to include shielding that generally surrounds detector crystal 14 to reduce the detection of radiation from surrounding non-target tissue, such as the injection site for the targeting agent. Accordingly, an aft shield 24 may be installed in housing 12 proximate printed circuit board 16, as shown in FIG. 1. A side shield 26 may also be made part of housing 12, generally surrounding detector crystal 14 as shown in FIG. 1.

Detector crystal 14 is preferably made of cadmium zinc telluride or any other semiconductor material suitable for detecting photon radiation, such as cadmium telluride (CdTe). Alternatively, any suitable scintillating material may be used including, but not limited to, cesium iodide. As shown in FIG. 1, detector crystal 14 includes a cathode 28, an anode 30 spaced apart from the cathode, and an edge 32 extending between the cathode and the anode. Detector crystal 14 is preferably situated within housing 12 with cathode 28 adjacent housing aperture 18, as shown in FIG. 1.

In the example embodiment of FIG. 1, detector crystal 14 is secured to housing 12 by one or more supports 34; however, the mechanical details of securing detector crystal 14 and printed circuit board 16 are not critical. Furthermore, the construction details of the components of probe 10 may be varied as desired, except as noted herein.

In one embodiment of the present invention ECD 20 is made from lead material of a suitable thickness, such as about 0.030 inch, although thinner or thicker materials may be selected. Alternate materials may also be selected separately or in combination with lead and/or each other including, without limitation, tantalum, platinum, gold, and bismuth.

In one embodiment of the present invention, aft shield 24 is made from tungsten material. However, alternate suitable materials or alloys may be selected. Selected materials are preferably those whose K-alpha secondary emissions are outside a predetermined energy acceptance window to be detected, so that K-alpha contributions from aft shield 24 are excluded from the measurement of the primary radiation target.

In one embodiment of the present invention, side shield 26 is made from tungsten material. However, alternate suitable materials or alloys may be selected. Selected materials are preferably those whose K-alpha secondary emissions are outside a predetermined energy acceptance window to be detected, so that K-alpha contributions from side shield 26 are excluded from the measurement of the primary radiation target.

A covering material 36 may be situated facially adjacent ECD 20 and/or any other appropriate portions of probe 10 to prevent human contact therewith. An example covering material may be anodized aluminum, among others.

In operation, ECD 20 is stimulated by energy emitted from a source of primary photon emission radiation and fluoresces, "converting" the received primary photon emission radiation to a corresponding secondary emission at a lower energy level. This conversion is defined herein as a K-alpha response that occurs when an incoming photon from primary target radiation collides with an electron within the detector 14, adding energy to the electron and pushing it to a higher energy state. When a higher-energy electron subsequently falls back into a lower-energy vacancy it emits a new (lower-energy) K-alpha photon, effectively converting the higher-energy target radiation to lower-energy K-alpha radiation. Detector crystal 14 generates an electrical signal representative of the amount of target emissions received through housing aperture 18.

The energy level of the secondary emission may be approximated using Equation 1, an empirical expression of Moseley's Law:

$$eV_{k\alpha} = 10.2(Z-1)^2 \quad \text{Equation 1}$$

where:
$eV_{k\alpha}$ is the energy level of photon emissions, measured in electron volts; and
Z is the atomic number of ECD 20.

Figure 2:
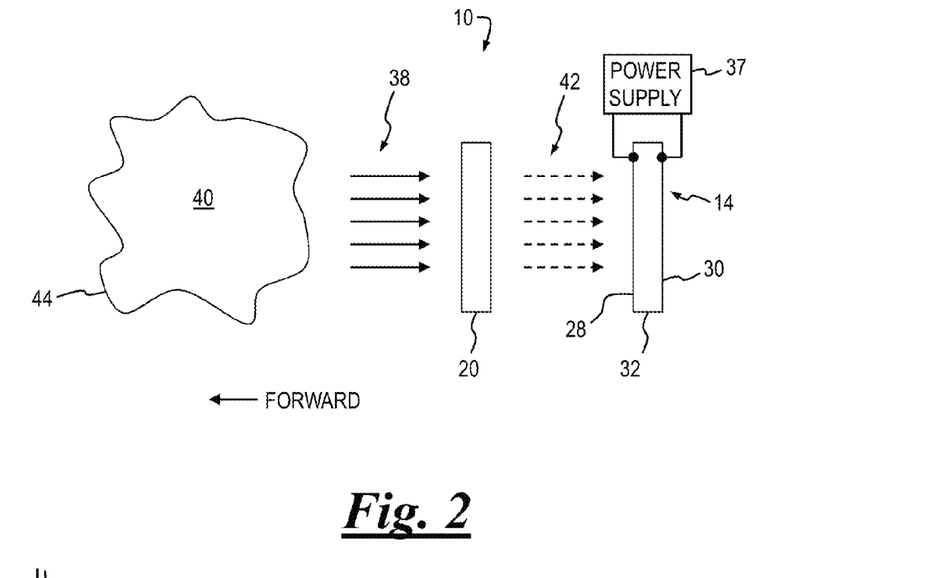
FIG. 2 is a schematic diagram of the probe of FIG. 1.
Figure 3:
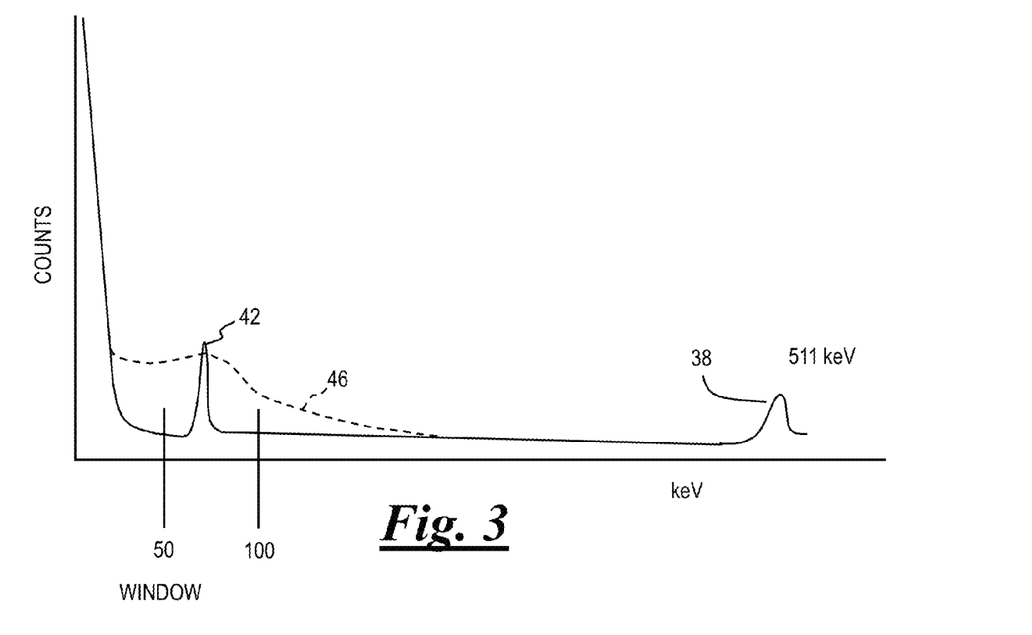
FIG. 3 is a graph showing a secondary photon emission measured by the probe of FIG. 1.

With reference to FIGS. 1, 2, and 3 in combination, an example embodiment with lead (Atomic Symbol Pb) selected for ECD 20 will now be described. First, Equation 1 is computed for lead, which has an Atomic Number equal to 82, resulting in Equation 2:

$$66.922 = 10.2(82-1)^2 \quad \text{Equation 2}$$

As shown schematically in FIG. 2, a power supply 37 is coupled to detector crystal 14 and configured to establish a polarized electrical field across the detector crystal. Primary photon emissions 38 from a radiation emitter 40 (such as generated by PET procedures) stimulate ECD 20, made of lead in this example. ECD 20 fluoresces, producing a secondary emission 42 that in effect converts the primary photon emissions to the secondary emission. Secondary emission 42 is detected by detector crystal 14. This is shown graphically in FIG. 3.

For reference, Mosely's formula may also be adapted from Bohr's formula, resulting in Equation 3 shown below:

$$f = v = \frac{m_e q_e^4}{8h^3 \epsilon_0^2}\left(\frac{3}{4}\right)(Z-1)^2 = (2.48 * 10^{15} \text{ Hz})(Z-1)^2$$

where:

| | |
|---|---|
| f = the frequency of the main or K x-ray emission line | Z = atomic number |
| v = frequency of characteristic radiation | $q_e$ = charge of an electron |
| $m_e$ = mass of an electron | $\epsilon_o$ = permittivity of free space |
| h = Planck's constant | |

The "directionality" of probe 10 refers to its ability to receive photon emissions 38 through housing aperture 18 and to reject emissions lateral to or aft of the probe. A probe having high directionality is able to more precisely differentiate boundaries 44 of radiation emitter 40. ECD 20, which is placed between photon emitter 40 and detector crystal 14, in effect converts the energy level of the primary photon emissions from emitter 40 to secondary emissions 42 at a lower energy level. This greatly increases detector crystal 14 efficiency without the need to employ relatively thick detector crystals. The use of a thinner detector crystal 14 yields a number of major novel advantages. Firstly, the exposed area of edge 32 of the thinner detector crystal 14 (FIGS. 1 and 2) is much smaller than with thicker crystals, greatly reducing the need for thicker side shielding to achieve desirable probe 10 directionality. This reduction of shielding thickness facilitates a smaller device, allowing for use of probes in applications where space is limited.

Furthermore, the energy conversion characteristic of ECD 20 allows the use of a not-shown signal preamplifier (used to amplify the output signal from detector crystal 14) of greatly reduced dynamic range as compared to current photon emission measuring systems because it need only respond to the lower secondary energy emissions 42 from ECD 20 and does not need to accommodate the higher energy photon primary emissions 38 produced by radiation emitter 40.

In addition, it is known that relatively thick CZT detector crystals 14 are difficult to manufacture and are expensive. Thinner CZT detector materials for K-alpha based radiation (i.e., secondary emission 42) detecting devices are much less expensive to manufacture than current designs. The higher the energy level of the radiation to be detected, the more the manufacturing cost will be reduced by the present invention. Further details of example signal preamplifiers may be found in the aforementioned U.S. patents incorporated herein by reference, although the present invention is not limited to use with such preamplifiers.

It should be noted that K-alpha secondary emissions 42 emitted by ECD 20 are of fixed energy level regardless of the radionuclide to be measured. Thus, a K-alpha-based device is "universal" in that it is compatible with any targeting agent with primary emissions 38 that are more energetic than the relatively low energy of the K-alpha secondary emission 42 response.

The migration of freed electrons within detector crystal 14 CZT material is facilitated by providing an electrical field across cathode 28 and anode 30 of the detector, the electrical field preferably having a polarity as shown in FIG. 1. Establishing this electrical field across a relatively thick detector 14 requires a relatively high bias voltage to achieve rapid charge migration and avoid charge entrapment in areas of impurity in the crystal material, typically at least 40 volts per millimeter of thickness. This can result in a bias voltage in excess of a thousand volts. In contrast, in the present invention the use of a relatively thin CZT element (1.5 mm, for example) for detector crystal 14 operates well with a relatively low voltage (60 volts, for example) applied across the detector crystal, thereby reducing the necessary electrical insulation thicknesses and clearances within probe 10.

In some embodiments of the present invention probe 10 may be constructed with detector crystal 14 oriented opposite that shown in FIG. 1, that is, with cathode 28 adjacent printed circuit board 16 and anode 30 adjacent housing aperture 18. Likewise, ECD 20 may be alternatively be situated anywhere aft of detector crystal 14 and forward of shield 24, as will be discussed further below. With reference again to FIG. 2 it can be seen that photon emissions 38 stimulate ECD 20, causing the generation of secondary emissions 42. The secondary emissions 42 pass through cathode 28 of detector crystal 14 and toward anode 30. This arrangement provides optimal spectral performance of the electrical signal generated by detector crystal 14. A characteristic of optimal spectral performance includes energy level discrimination wherein signal peaks are easily discernable and have a relatively narrow spectrum, such as illustrated pictorially by secondary emissions 42 in FIGS. 3, 5 and 6. Non-preferred arrangements of ECD 20, cathode 28 and anode 30 may result in detector 14 electrical signals having less than optimal energy level discrimination, as illustrated pictorially by a broken line 46 in FIG. 3.

In addition, as previously noted, any shielding (24, 26) that is used is preferably made from a material whose K-alpha secondary emissions 42 are outside the energy acceptance window (see FIG. 3) for the nuclide to be detected so that any K-alpha contributions from the shielding will not be included in the measurement of the primary radiation target.

Figure 4:
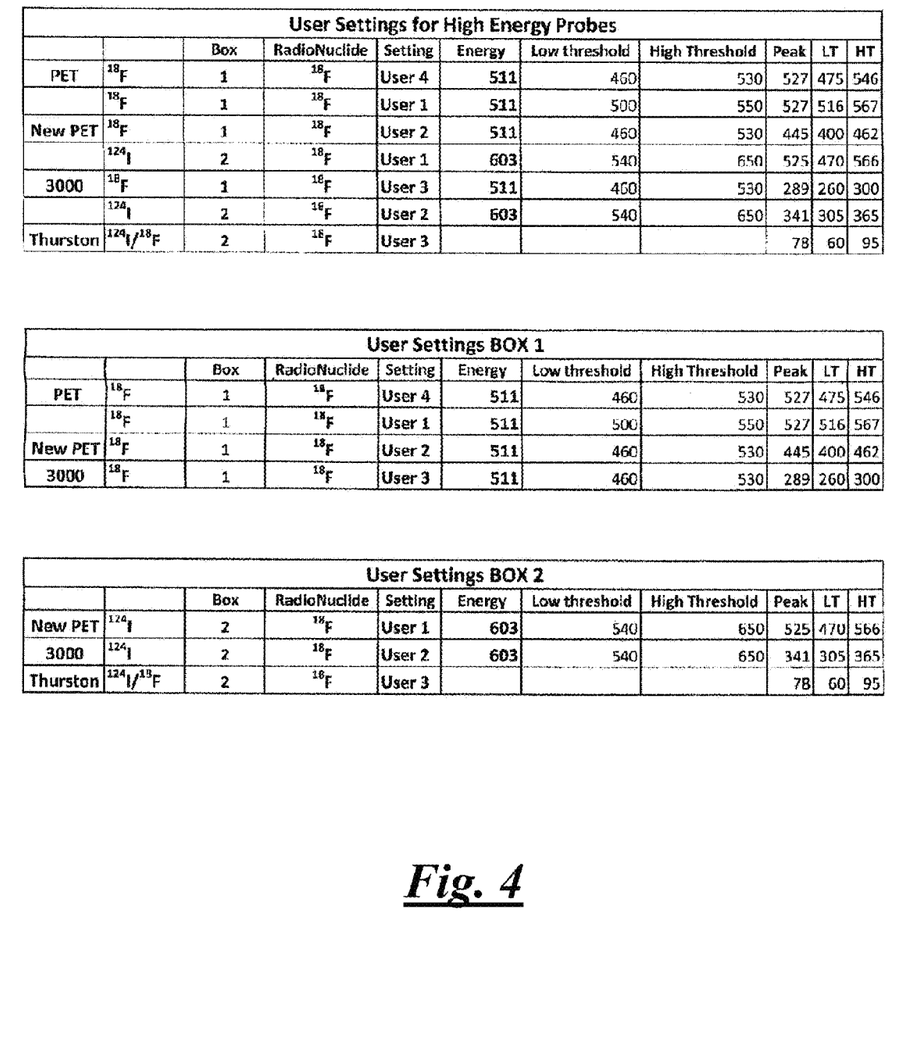
FIG. 4 shows tables of example probe settings.
Figure 5:
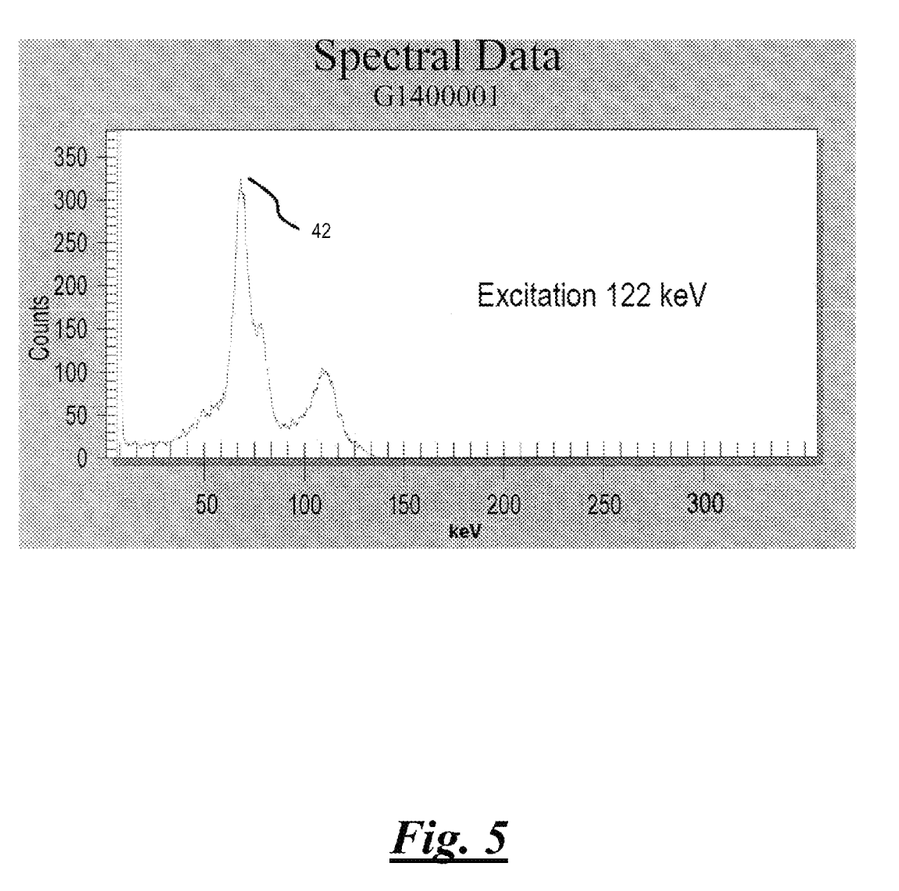
FIG. 5 shows example spectral data for the probe of FIG. 1 in response to a 122 keV radiation source.
Figure 6:
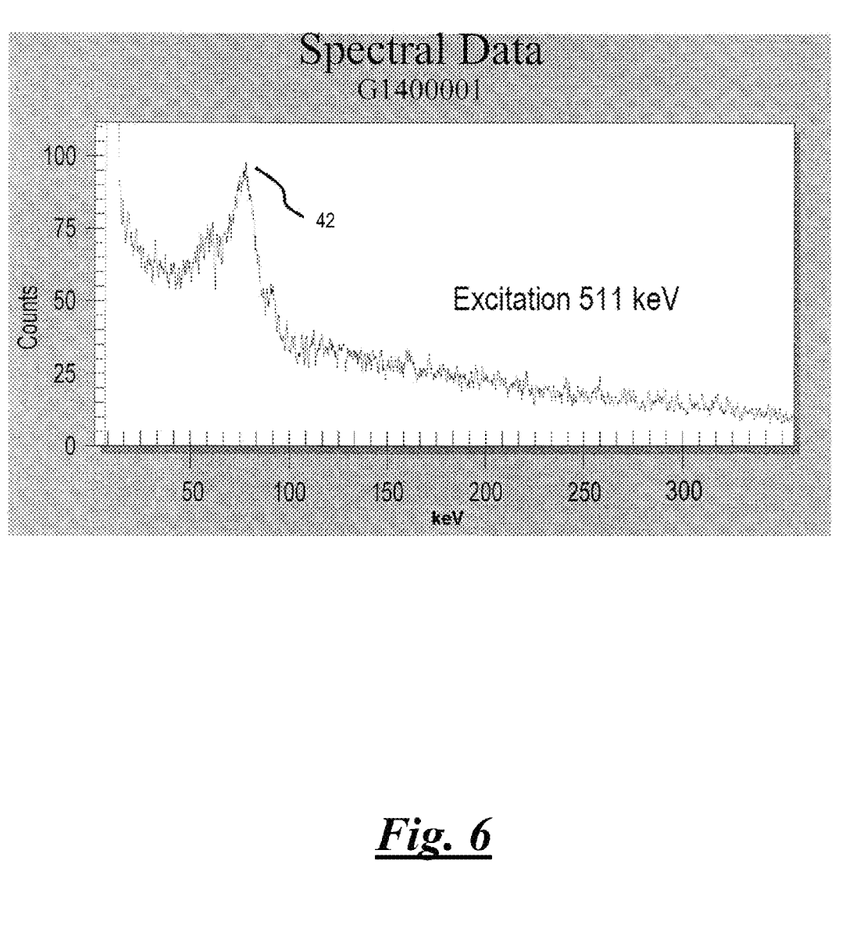
FIG. 6 shows example spectral data for the probe of FIG. 1 in response to a 511 keV radiation source.

FIGS. 4, 5, and 6 are probe 10 settings and spectral data graphs of typical test results with a probe 10. As can be seen from FIGS. 5 and 6, secondary emission 42 peaks are coincident despite varying levels of energy source. Thus, a K-alpha-based device is "universal" in that it is compatible with any targeting agent with primary emissions 38 that are more energetic than the relatively low energy of the K-alpha secondary emission 42 response. These figures are for general illustration only and are not considered to be limiting in any way.

Figure 7:
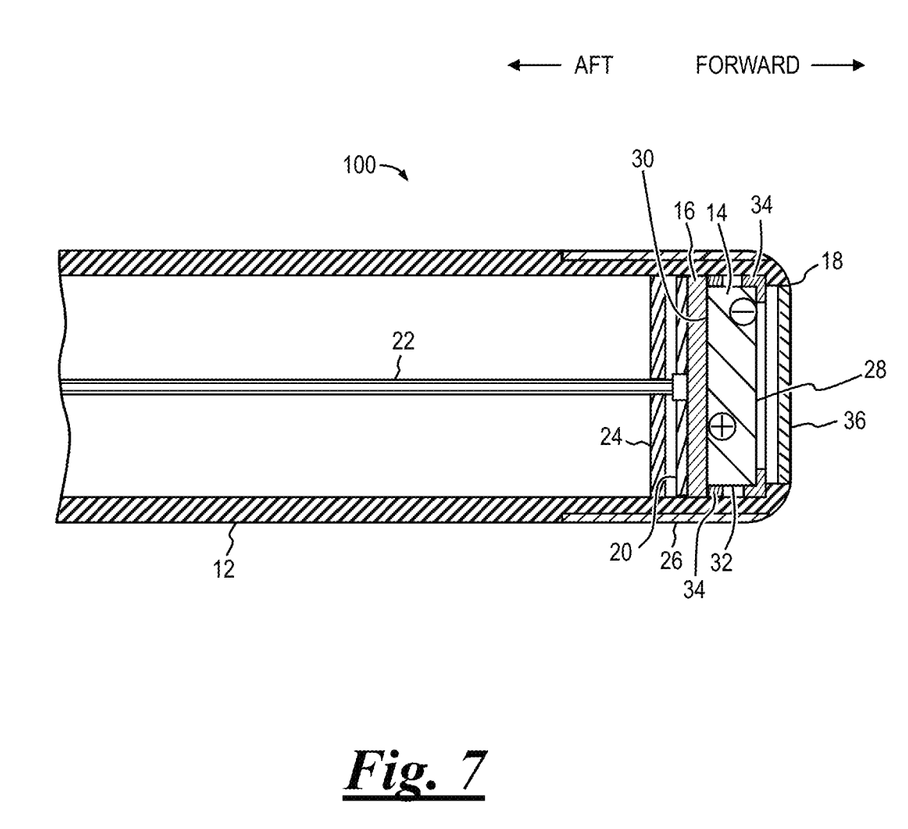
FIG. 7 is a view in section of a probe for detection of photon emissions according to another embodiment of the present invention.

The general arrangement of a probe 100 for detecting photon emissions is shown in FIG. 7 according to another embodiment of the present invention. Probe 100 comprises a housing 12. A detector crystal 14, which may be mounted to a printed circuit board 16, is disposed within housing 12 proximate an aperture 18 of the housing. An ECD 20 is coupled to housing 12, aft of and proximate detector crystal 14. A set of leads 22 provides electrical communication with printed circuit board 16 and detector crystal 14, leads 22 being connected to a suitable radiation detection apparatus, such as (but not limited to) those disclosed in one or more of the aforementioned patents. The general arrangement of probe 100 is otherwise similar to probe 10 and thus will not be detailed further.

Figure 8:
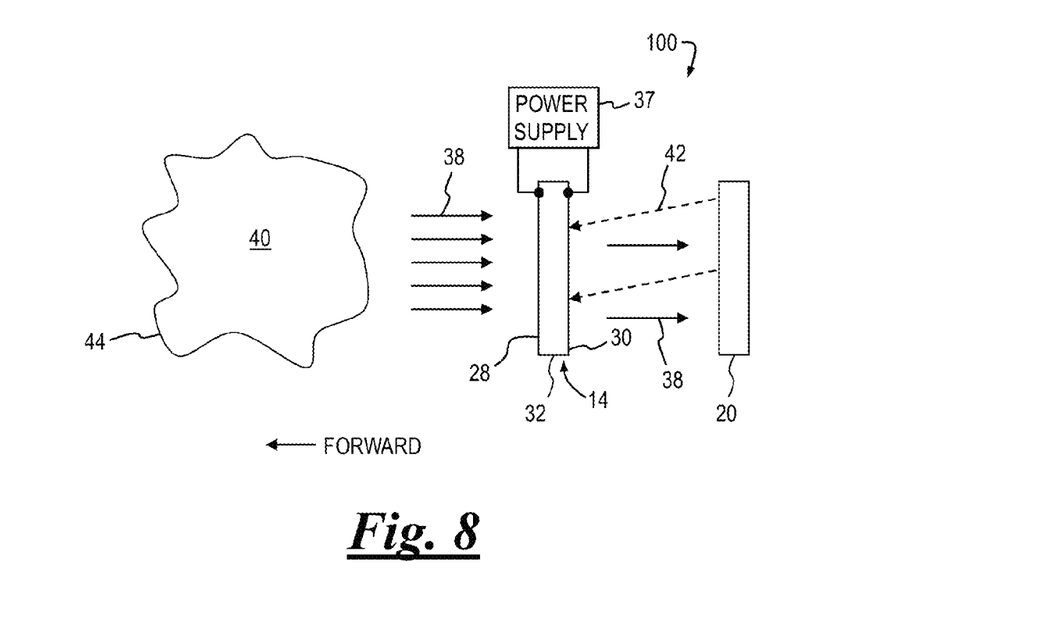
FIG. 8 is a schematic diagram of the probe of FIG. 7.

As shown schematically in FIG. 8, a power supply 37 is coupled to detector crystal 14 and configured to establish a polarized electrical field across the detector crystal. Primary photon emissions 38 from a radiation emitter 40 pass through a detector crystal 14 and stimulate ECD 20. ECD 20 fluoresces, producing a secondary emission 42 that in effect converts the primary photon emissions to the secondary emission. Secondary emission 42 is detected by detector crystal 14. This is shown graphically in FIG. 3.

Figure 9:
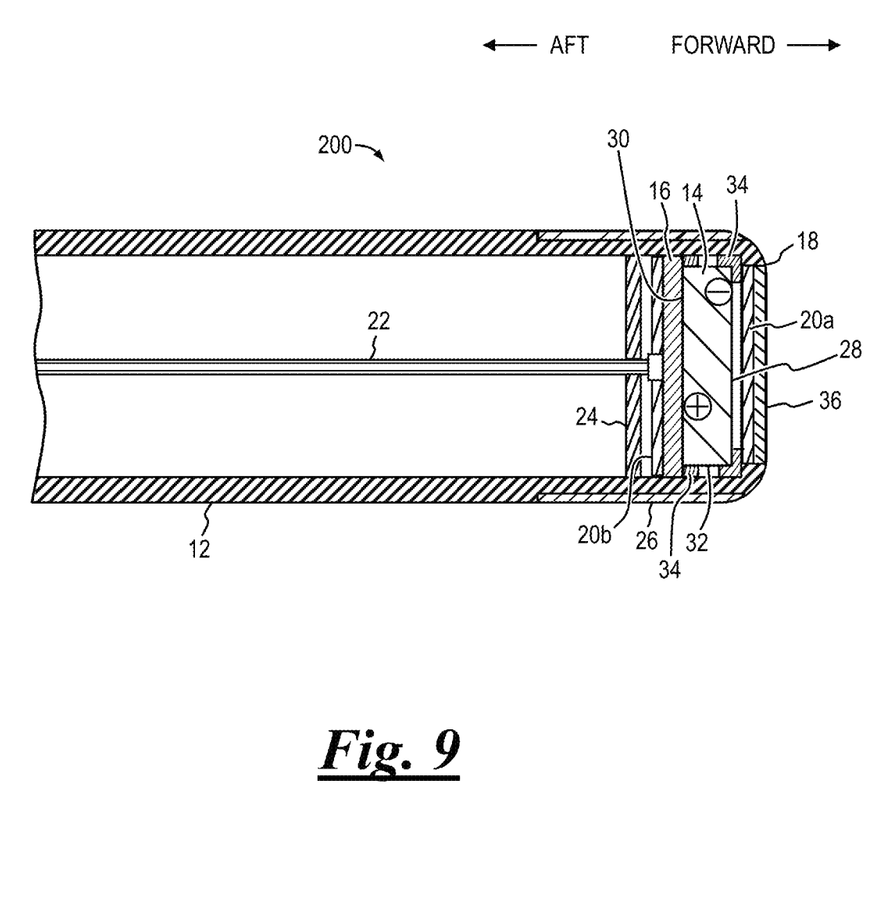
FIG. 9 is a view in section of a probe for detection of photon emissions according to yet another embodiment of the present invention.

The general arrangement of a probe 200 for detecting photon emissions is shown in FIG. 9 according to yet another embodiment of the present invention. Probe 200 comprises a housing 12. A detector crystal 14, which may be mounted to a printed circuit board 16, is disposed within housing 12 proximate an aperture 18 of the housing. A first ECD 20a is coupled to housing 12, proximate detector crystal 14 and substantially closing off aperture 18. A second ECD 20b is coupled to housing 12, aft of and proximate detector crystal 14. A set of leads 22 provides electrical communication with printed circuit board 16 and detector crystal 14, leads 22 being connected to a suitable radiation detection apparatus, such as (but not limited to) those disclosed in one or more of the aforementioned patents. The general arrangement of probe 200 is otherwise similar to probe 10 and thus will not be detailed further.

Figure 10:
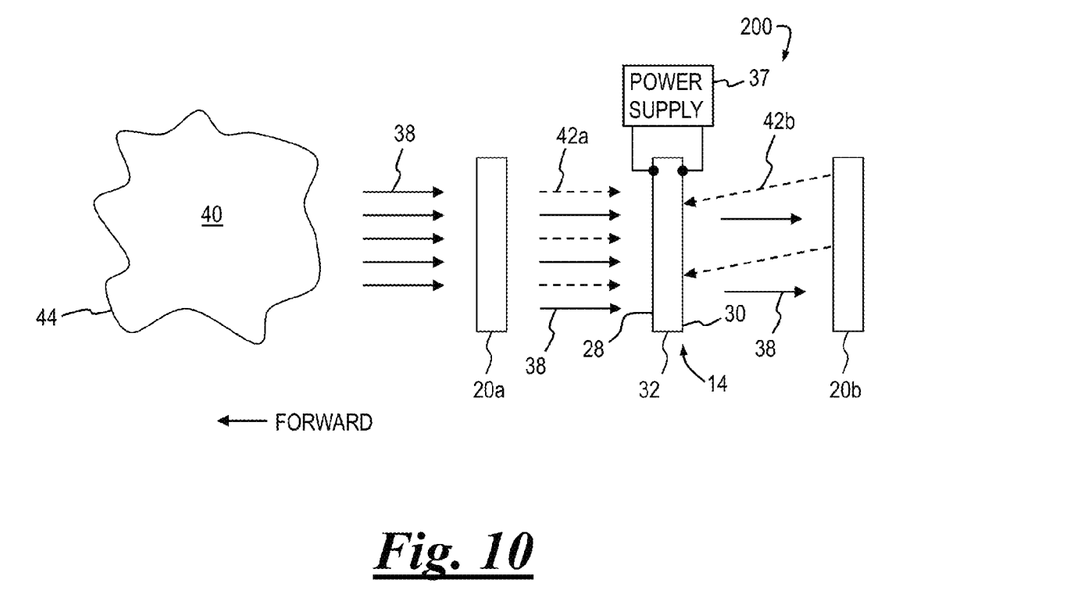
FIG. 10 is a schematic diagram of the probe of FIG. 9.

As shown schematically in FIG. 10, a power supply 37 is coupled to detector crystal 14 and configured to establish a polarized electrical field across the detector crystal. Primary photon emissions 38 from a radiation emitter 40 stimulate first ECD 20a, made of lead in this example. ECD 20a fluoresces, producing a secondary emission 42a that in effect converts the primary photon emissions to the secondary emission. In addition, some primary photon emissions 38 from radiation emitter 40 pass through first ECD 20a and detector crystal 14 and stimulate ECD 20b. ECD 20b fluoresces, producing a secondary emission 42b that in effect converts the primary photon emissions to the secondary emission. Secondary emissions 42a, 42b are detected by detector crystal 14. This is shown graphically in FIG. 3.

It should be noted that the present invention is not limited to medical applications. For example, the present invention is envisioned to be used to advantage in various security, agricultural, industrial, or any other applications involving radiation detection and/or measurement.

While this invention has been shown and described with respect to a detailed embodiment thereof, it will be understood by those skilled in the art that changes in form and detail thereof may be made without departing from the scope of the claims of the invention.

What is claimed is:

1. A probe for detecting K-alpha photon emissions, the probe comprising:
    a housing having a housing end configured for receiving energy from a primary photon emission source;
    an energy conversion device disposed within the housing, the energy conversion device comprising a material configured to convert energy received from the primary photon emission source to a corresponding secondary K-alpha emission; and
    a detector crystal disposed within the housing, the detector crystal configured to receive the secondary K-alpha emission and generate a signal representative of energy received through the housing end.

2. The probe of claim 1 wherein the housing end further comprises an aperture through which energy from the primary photon emission source is received.

3. The probe of claim 1 wherein the detector crystal comprises cadmium zinc telluride.

4. The probe of claim 1 wherein the detector crystal comprises cesium iodide.

5. The probe of claim 1 wherein the energy conversion device comprises a metal.

6. The probe of claim 1 wherein the energy conversion device comprises at least one of lead, tantalum, tungsten, gold and bismuth.

7. The probe of claim 1, further comprising a side shield.

8. The probe of claim 7 wherein the side shield substantially surrounds an edge of the detector crystal.

9. The probe of claim 1, further comprising a shield aft of the detector crystal.

10. A probe for detecting K-alpha photon emissions, comprising:
    a housing having a housing end;
    a cadmium zinc telluride detector crystal having a cathode and an anode spaced apart from the cathode, the detector crystal disposed within the housing with one of the cathode and the anode adjacent to the housing end; and
    a metallic member disposed within the housing intermediate the detector crystal and the housing end, the metallic member being configured to convert energy directed through the housing end from a source of primary photon emission radiation to a corresponding secondary K-alpha emission within a predetermined emission energy acceptance window.

11. The probe of claim 10, further comprising a side shield disposed to shield an edge of the detector crystal.

12. The probe of claim 10, further comprising a shield proximate the detector crystal.

13. The probe of claim 10, further comprising a power supply coupled to the detector crystal and configured to establish a polarized electrical field across the detector crystal.

14. The probe of claim 10, further comprising a cover adjacent to the metallic member.

15. The probe of claim 10 wherein the metallic member comprises at least one of lead, tantalum, tungsten, bismuth, and gold.

16. A probe for detecting K-alpha photon emissions, comprising:
    an energy conversion device comprising a metal and configured to convert energy from a source of primary photon emission radiation to a corresponding secondary K-alpha emission within a predetermined emission energy acceptance window; and
    a detector crystal having a cathode, an anode spaced apart from the cathode, and an edge extending between the cathode and the anode, the detector crystal disposed to receive the K-alpha emission, and the detector crystal configured to generate an electrical signal representative of the amount of primary photon energy received by the energy conversion device.

17. The probe of claim 16, further comprising a side shield disposed to shield the edge of the detector crystal.

18. The probe of claim 16, further comprising a shield aft of and proximate the detector crystal.

19. The probe of claim 16 wherein the detector crystal comprises cadmium zinc telluride.

* * * * *